United States Patent [19]

Wilson, Jr. et al.

[11] Patent Number: 4,632,668
[45] Date of Patent: Dec. 30, 1986

[54] VENTRICULAR CATHETER

[75] Inventors: John K. Wilson, Jr.; Tae S. Park, both of Charlottesville, Va.

[73] Assignee: University of Virginia Alumni Patents Foundation, Charlottesville, Va.

[21] Appl. No.: 688,003

[22] Filed: Dec. 31, 1984

[51] Int. Cl.$^4$ .......................................... A61M 27/00
[52] U.S. Cl. .......................................... 604/8; 604/49
[58] Field of Search ...................... 604/8–10, 604/49, 54; 128/348.1

[56] References Cited

U.S. PATENT DOCUMENTS

| | | | |
|---|---|---|---|
| 3,623,484 | 12/1971 | Schulte | 604/8 |
| 4,375,816 | 3/1983 | Labianca | 604/8 |
| 4,382,445 | 5/1983 | Sommers | 604/8 |
| 4,578,057 | 4/1986 | Sussman | 604/9 |

FOREIGN PATENT DOCUMENTS 0395072 8/1973 U.S.S.R. .................................. 604/8

Primary Examiner—Dalton L. Truluck
Assistant Examiner—Karen L. Kaechele
Attorney, Agent, or Firm—James C. Wray

[57] ABSTRACT

An adjustable ventricular catheter is disclosed. This invention has a proximal catheter in which a distal catheter telescopically slides. The distal catheter is prevented from separating from the proximal catheter in the maximum extended position by locking means. The distal catheter may be further extended, forshortened, or removed by means of a stylet inserted into the hollow of the proximal and distal catheters with flexible projections on the end of the stylet capturing drain holes on the closed end of the distal catheter such that sliding of the stylet moves the distal catheter in a telescoping relationship within the proximal catheter.

24 Claims, 10 Drawing Figures

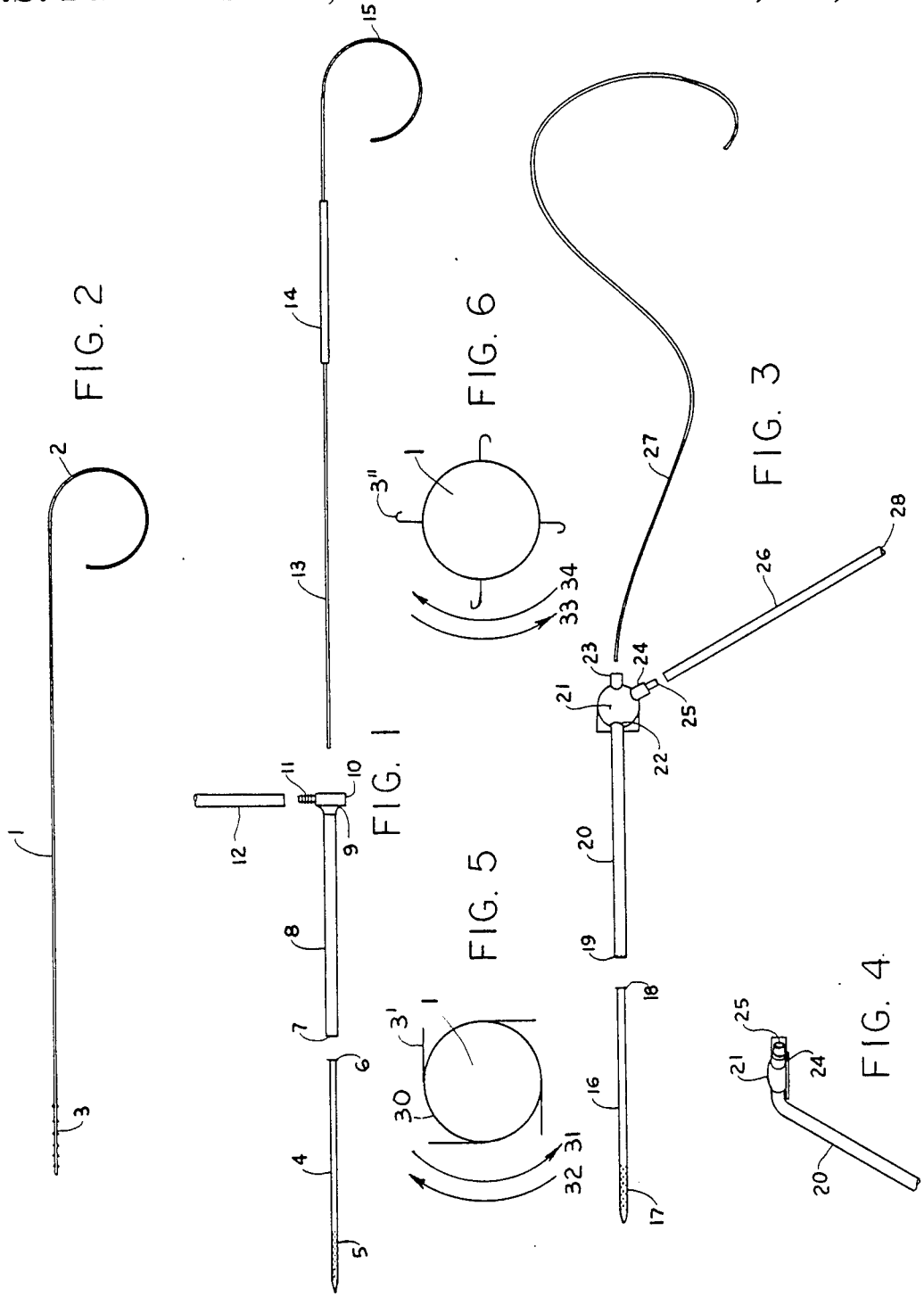

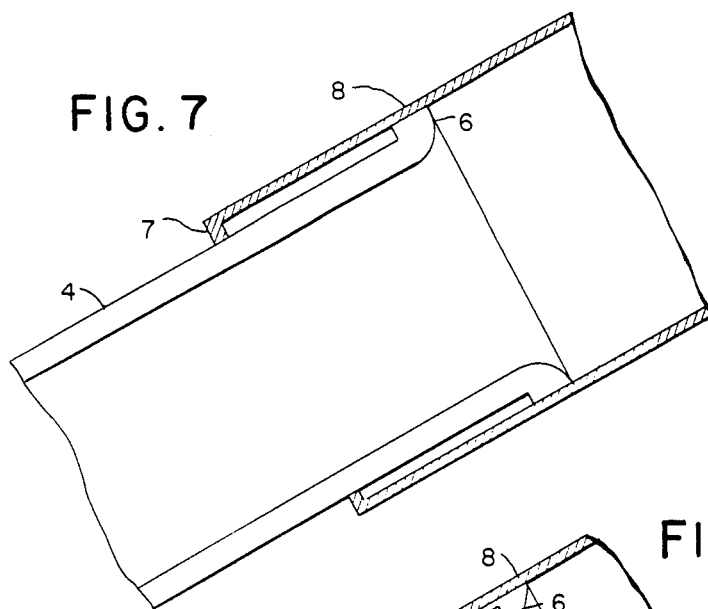
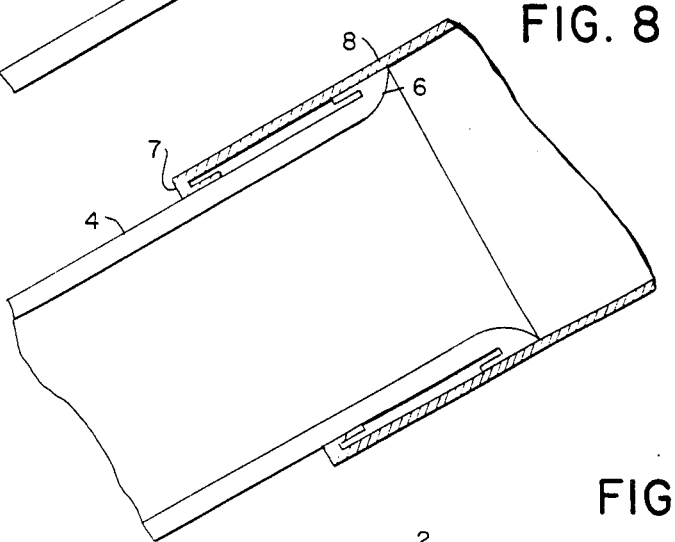
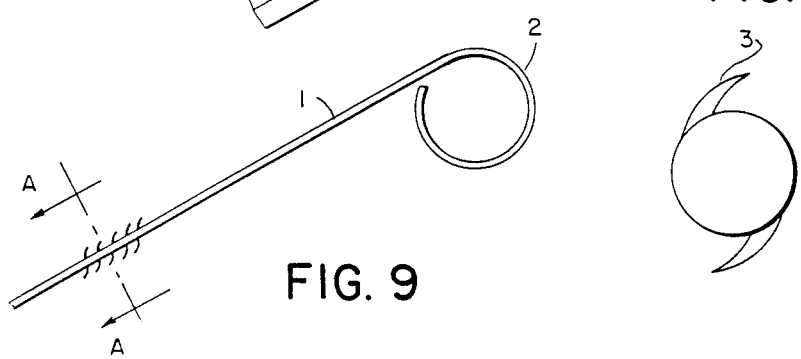

VENTRICULAR CATHETER

BACKGROUND OF THE INVENTION

1. Field of the Invention

The invention relates to surgical devices for transferring fluids from within the area of the body having flow control means and antisyphon means. Such devices may include means for introducing or removing material from the body for therapeutic purposes. The means for removing material in the body may include piercing conduits inserted into the body. Such piercing conduits is meant to contemplate catheters having flexible catheter guides. More in particular, the invention relates to ventricular catheters used in the treatment of hydrocephalus.

2. Background Art

Ventricular catheters have been implanted since 1952 as components of cerebral-spinal fluid (csf) shunt systems. The Pudenz ventricular catheter currently in use is a silicon elastimer varying from 1.2 mm to 1.4 mm internal diameter and from 2.2 mm to 2.5 mm outside diameter. The tip of the catheter contains a radiopaque plug allowing introduction of the catheter with a stiff wire stylet. The problem with this and all ventricular catheters currently in use is their inability to adjust in length according to therapeutic needs in the treatment of hydrocephalus. Currently, catheters are implanted using standard operative procedures. When the catheter needs to be lenghthened, the patient undergoes a surgical procedure to remove and replace the catheter. The present invention eliminates this added surgical procedure to remove and replace the catheter.

SUMMARY OF THE INVENTION

Hydrocephalus is a condition marked by an excessive accumulation of fluid dilating the cerebral ventricles, thinning the brain and causing a separation of cranial bones. Treatment of this disease includes the use of ventricle catheters to drain off this collection of fluid. A problem arises when the ventricular catheter must be lengthened to better draw off collecting fluid.

At the present time, ventricular catheters must be replaced if they are to be lengthened, thus involving additional surgical procedures. The procedure requires removal and reimplantation in a neurosurgical procedure. These shunt revisions are a common problem estimated to be about one third of the pediatric neurosurgical practice.

The present invention allows lengthening and/or replacement of the ventricular catheter under fluoroscopy without surgical procedure.

The Park/Wilson extendable-retractable ventricular catheter is a system designed to facilitate shunting of cerebral spinal fluid in the treatment of hydrocephalus. The system is composed of:

(1) an implantation stylet;
(2) a distal ventricular catheter;
(3) a proximal catheter and introduction port fabricated as one unit with or without a reservoir; and
(4) an extension/retraction wire.

When used as a component of a CSF shunting system, the invention allows for extension, retraction or replacement of the distal ventricular catheter in a relatively noninvasive procedure using fluoroscopy.

The invention is an extendable/retractable ventricular catheter which is essentially a two-piece telescoping assembly with a distal catheter slideably extending from within a proximal catheter. The proximal catheter is basically a hollow tube or cannula which is large enough in circumference to slideably receive the distal catheter which again is a hollow tube or cannula. The distal catheter is closed on its distal end upon which is provided perforations for draining. When this distal catheter is extended to its maximum length from within the proximal catheter, the two pieces are prevented from coming apart by the distal catheter having an external locking means and the proximal catheter having internal locking means which prevents the distal catheter from being pulled or pushed completely outside of the proximal catheter. The external locking means on the distal catheter is essentially a lip radially extending outward. The internal locking means on the proximal catheter may be a constriction in the lumen. At the end of the proximal catheter opposite the end from the which the distal catheter extends, is located an access port and a discharge port. The access port is directly aligned and contiguous with the lumen of the proximal catheter and allows for insertion of the distal catheter, closed end first, an implantation stylet or an extension/retraction stylet. Coming off the side of the access port is a discharge port which allows for the discharge of fluid being drained through the distal catheter into the proximal catheter. The access port and discharge port may be located on a reservoir which is assembled upon the end of the proximal catheter.

Implantation of this device is a relatively routine procedure. The two piece catheter is implanted in its unextended position initially. That is, the distal catheter is positioned inside the proximal catheter initially. When setting the distal catheter in position, an implantation stylet is used which is essentially a long wire having a handle on one end. A depth gauge is used with this stylet which comprises basically a hollow tube through which the wire extends. The gauge is larger in circumference than the access port and will only allow a certain amount of the implantation stylet to pass through the proximal catheter. The implantation stylet will push the closed end of the distal catheter in an extending motion and the depth gauge will govern the extent of the distal catheter projecting beyond the proximal catheter. Upon setting the distal catheter into position, the implantation stylet is removed, the access port is closed off, a discharge tube is attached to the discharge port on the proximal catheter and the fluid is then drained.

To effect a position change of the distal catheter, either an extension or retraction stylet is used. The retraction stylet is essentially an elongated wire having barbs on one end. The retraction stylet is inserted into the catheter by way of the access port. The barbs are projections extending in an outward direction from the wire. They are situated on the wire such that when the wire is rotated in one direction within the distal catheter (near the proximal end thereof), the barbs will not catch the walls. This movement is necessary to insure insertion of the wire. When the wire is sufficiently within the distal catheter, rotation is reversed, the barbs catch on the Silastic plastic of the distal catheter, and the wire may be pulled out through the proximal catheter with the distal catheter in accompaniment. When the proximal catheter has a flexible reservoir, a more flexible stylet should be used where it can be inserted into the access port, across the hollow of the reservoir and into the lumen of the proximal catheter. Extension of the distal catheter would be accomplished with a smooth stylet pushing the end of the distal catheter further within the cavity of a cerebral ventricle. The ventricular catheter preferably consists of a silicone elastimer which is compatible with in vivo procedures.

It is an object of this invention to provide an extendable/retractable ventricular catheter.

It is another object of this invention to provide a device which circumvents the need for added surgical procedures in the treatment of hydrocephalus beyond the initial catheter implantation.

It is another object of this invention to provide a two piece telescoping extendable/retractable ventricular catheter which has locking means preventing the distal and proximal portions from separating in the maximal extended position.

It is still another object of this invention to improve the therapy for hydrocephalus.

BRIEF SUMMARY OF THE DRAWINGS

FIG. 1 is an exploded side view of one embodiment of the invention.

FIG. 2 is a side view of the extension/retraction stylet.

FIG. 3 is an elevated exploded view of another embodiment of the invention.

FIG. 4 is a side view of the access port and discharge port of FIG. 3.

FIG. 5 is a cross-section of FIG. 2 along line 29—29.

FIG. 6 is an alternate embodiment of FIG. 5.

FIG. 7 is a cross sectional view showing end portions of proximal and distal cannulas defining locking means.

FIG. 8 is an alternative embodiment of FIG. 7.

FIG. 9 shows a detail description of one embodiment of the extension/retraction stylet.

FIG. 9a is a cross sectional view taken along line a—a of FIG. 9.

DETAILED DESCRIPTION OF THE INVENTION

The treatment of hydrocephalus involves the insertion of a permanent apparatus for draining the cerebral ventricles. A burr hole is made in the skull and a catheter or shunt device is inserted through parts of the brain into the ventricles to drain off the fluid. The device is usually an assemblage of tubes extending from a drainage end located within the brain outward to a reservoir or access/drainage port which may reside anchored within the burr hole itself. The reservoir or access drainage port may also be flush mounted on the skull with the tube bending down through the burr hole at an angle. These drainage devices or ventricular catheters are usually implanted subcutaneously with the drainage being routed back into the body for absorption purposes.

Periodically, the length of the catheter must be extended. Prior to the invention, neurological surgery was needed to remove and replace the tubing. This procedure involved opening the scalp and pulling the old tubing out through the burr hole and inserting new tubing. Consequently, the brain tissues were disturbed. The invention eliminates this neurological surgery by the permanent installation of a proximal catheter. This tubing spans the distance between the skull and the ventricles. Telescoping from within this permanent tubing is the distal catheter made of a softer more flexible material. This distal catheter may be manipulated to extend to any desired length beyond the proximal catheter.

The access port to the proximal catheter on the skull surface provides access not only to distal catheters and various manipulatory stylets but also to anything. Television cameras, lasers, and medicines are just a few of the items for which the proximal catheter provides access to the inner brain.

The invention will now be set out in its preferred mode by referring specifically to the drawings. Referring to FIG. 1, the preferred mode of the invention without a reservoir is shown. The invention comprises a proximal catheter 8 which is a hollow cannula adapted to slideably receive distal catheter 4 also a hollow cannula. The two cannulas are preferably made from a silicone elastimer compatible with human in vivo situations. The telescoping proximal and distal catheters may be assembled by inserting the distal catheter closed end 5 first through access port located on end 10. Distal catheter 4 has external locking means 6 comprising an annular lip extending radially outward. This lip which approximates the lumen diameter of proximal cannula 8 and interacts with internal locking means 7 located within the lumen of proximal cannula 8. The internal locking means comprises a constriction of any suitable fashion in the lumen such that when the distal catheter is being extended from within proximal cannula beyond end 7, the lip 6 is prevented from exiting the end 7 by means of the constriction in the lumen located in cannula 8. Initial implantation of this catheter has the catheter in its unextended position, with the distal catheter positioned for the most part inside of the proximal catheter. The implantation stylet 13 is inserted in the access port and abutted against the closed end 5 of distal catheter 4. The implantation stylet 13 is then urged through the proximal catheter to the extent allowed by depth gauge 14. Whereupon the distal catheter is extended to the extent desired and the implantation stylet 13 is withdrawn. The depth gauge 14 (bumper) comprises a rigid hollow tube larger in circumference than the access port. When the implantation stylet 13 is inserted through the depth gauge 14 and then inserted into the access port to position the distal catheter, depth gauge 14 buts up against the access port and prevents the implantation stylet 13 from being inserted more than the desired amount. Handle means 15 located on the implantation stylet 13 is the means by which depth gauge 14 stops the insertion of implantation stylet 13.

The distal catheter 4 is closed at end 5 as shown in FIG. 1 and is provided with perforations which allow for the incoming flow of fluid to be drained from the ventricle. The closed end of the distal catheter allows for the implantation stylet to move the distal catheter in an extending direction. The retraction stylet is preferably made of a wire or rigid material and has projections 3 on the end thereof.

The projections extend outwardly from the wire and are situated such that the rotation in one direction within the distal catheter is relatively free and allows for insertion of the wire within the distal catheter. When the barbs are inserted at least as far into the distal catheter as to be beyond the lip 6, then the wire may be rotated in the opposite direction where the barbs will grab the Silastic material comprising the catheter and allow for retraction back through the proximal catheter.

FIG. 5 presents an arrangement of barbs as does FIG. 6. FIG. 5 presents the barbs 3' as being tangentially connected 30 to the wire 1. The barbs may be flexible material which is bonded, welded, molded or machined onto the wire. The wire itself may be metal or plastic. When wire 1 is rotated in the direction of arcuate arrow 31, the barbs fail to catch the silastic material. When the wire 1 is rotated in the direction of arcuate arrow 32, the barbs catch the silastic material and the distal catheter may then be retracted.

FIG. 6 has a fishhook type arrangement. Hook 3" when rotated in the direction of arrow 33, will not catch the silastic material whereas rotation in the opposite direction 34 will catch the material to allow for retraction of the distal catheter.

Should the situation require a different distal catheter, all that would be required is for the retraction stylet to be inserted within the catheter whereupon projections 3 would capture the silastic material and the distal catheter may be pulled back through the proximal catheter and out the access port. A new distal catheter may then be inserted by way of an implantation stylet.

FIG. 7 shows in greater detail a preferred embodiment of the locking means. The distal catheter 4 is provided with external locking means 6. When fully extended, the external locking means 6 will abut internal locking means 7. The internal locking means 7 defines an end of proximal cannula 8.

FIG. 8 points out a slightly different embodiment of FIG. 7.

FIG. 9 shows another embodiment of the wire 1 in which the projections 3 are tangentially disposed about the outer surface of the wire 1 such that the projections are diametrically opposed and extend radially outwardly in opposite directions.

FIG. 3 offers an alternative embodiment having a reservoir 21 located on proximal catheter 20. The distal catheter in this embodiment is the same as in FIG. 1. That is, the distal catheter comprises a hollow cannula 16 closed on the end 17 having perforations. The distal catheter is also provided with the external outward radial annular lip 18 which catches upon a constriction in the lumen located at end 19 of cannula 20. Reservoir 21 is located upon end 22 of cannula 20. Reservoir 21 is an enlarged collecting area for fluid to be drained out of discharge port 24 having nipple 25 upon which discharge tube 26 may be attached for the draining of fluid out end 28. Access port 23 functions in the same way as access port on end 10 in FIG. 1. That is, distal catheter 16 may be inserted into and extracted from proximal catheter 20 by way of access port 23. A flexible extension stylet 27 for use with the proximal catheter having a reservoir 21 is shown. The flexible projections are not shown. It is to be understood that the extension/retraction stylet of FIG. 2 may be flexible as shown with stylet 27 in FIG. 3.

FIG. 4 shows a side view of the reservoir 21 having discharge port 24 with nipple 25 upon which discharge tube 26 may be fitted. The reservoir is shown to be an essentially flat outer structure.

Implantation of the ventricular catheter of FIG. 3 is essentially the same as in FIG. 1. The catheter is initially implanted with the distal catheter positioned inside the proximal catheter. Final positioning of the distal catheter is effected by use of an implantation stylet with a depth gauge as shown in FIG. 1. The implantation stylet is inserted through the catheter to the extent allowed by the depth gauge 14 whereupon distal catheter 16 is positioned according to the desired specifications. Further extension, forshortening or extracting of the distal catheter 16 is effected with an extension or retraction stylet having projections 3, in the manner as described above.

It is preferred that the proximal catheter, distal catheter, access port and discharge port all be made from a silicone elastimer compatible with human in vivo situations. The proximal catheter may be of a more rigid material than the distal catheter to better effect a telescoping relationship. The distal catheter may be more flexible than the proximal to facilitate positioning within the ventrical of the brain in a least harmful manner. Preferably, the distal catheter is provided with visualization means such that positioning may be monitored electronically. Barium impregnation of the distal catheter is one way to render the catheter visible to X-ray equipment. The discharge tube attaching to the discharge port may be of a rigid material. The discharge tube 12 of FIG. 1 may threadably engage a discharge port 11 provided with threads. The discharge tube 26 of FIG. 3 may merely fit upon nipple 25 adapted to receive discharge tube 26. The extension/retraction stylet as well as, the implantation stylet may be of any thin flexible wirelike material.

While the invention has been described by referring particularly to two embodiments, it is to be noted that the invention may vary in any obvious manner from the descriptions of the particular embodiments without departing from the scope and spirit of the invention. Accordingly, the spirit and scope of the invention is set out in the claims.

What we claim is:

1. An adjustable ventricular catheter, comprising:
   (a) a proximal cannula having a lumen and having first and second ends with said second end being further provided with internal locking means;
   (b) a distal cannula provided with a lumen, said distal cannula adapted to slide within said lumen of said proximal cannula in a telescopic relation, said distal cannula having first and second ends wherein said second end is closed and is provided with perforations, said first end having external locking means;
   (c) removable means, slideably received within the proximal cannula and extending to the distal cannula, for slideably adjusting the distal cannula within the proximal cannula, whereby one may set a desired length of the distal cannula extending beyond the second end of the proximal cannula with a maximum extension achieved by extending the second end of the distal cannula beyond the second end of the proximal cannula to a point where the internal locking means cooperates with the external locking means thereby providing further extension.

2. The device of claim 1 where said internal locking means further comprises a constriction in the lumen at the second end of the proximal catheter.

3. The device of claim 2 where the external locking means further comprises an annular outward radially extending lip.

4. An adjustable ventricular catheter kit, comprising:
   (a) an implantation stylet;
   (b) a distal ventricular catheter having a cannula and lumen with first and second ends, wherein said first end is provided with external locking means and wherein said second end is provided with a closure having perforations located thereon, said distal ventricular catheter being adapted to be slideably maneuvered within a proximal ventricular catheter, whereby a telescoping relationship between the distal catheter and the proximal catheter is established;

(c) a proximal ventricular catheter having a cannula and lumen with first and second ends wherein said second end has internal locking means adapted to cooperate with the external cooperating means when said distal catheter is extended telescopically to a maximal extent;

(d) an extension, retraction stylet.

5. The kit of claim 4 where the implantation stylet further comprises a depth gauge.

6. The kit of claim 5 wherein said depth gauge is a hollow tube of specific length through which the stylet extends.

7. The kit of claim 6 wherein said stylet is a wire.

8. The kit of claim 7 where said external locking means further comprises an annular radial outward extending lip.

9. The kit of claim 8 where said internal locking means further comprises a constriction in the lumen.

10. The kit of claim 9 where said first end of said proximal catheter has both an access port and a discharge port, wherein said access port is adapted to slideably receive said distal catheter first end first, the implantation stylet and an extension and retraction stylet.

11. The kit of claim 10 where said second end of said proximal catheter further comprises a reservoir upon which said access port and discharge port are located.

12. The kit of claim 11 wherein said extension/retraction stylet further comprises first and second ends with said first end being provided with handle means and second end being provided with adjustment means.

13. The kit of claim 12 where said adjustment means further comprises outward radially extending projections, whereby said projections are adapted to capture said distal ventricular catheter whereupon adjustments in the telescoping relationship between said distal catheter and said proximal catheter are effected.

14. An adjustable ventricular catheter, comprising:

(a) a proximal cannula having a lumen and having first and second ends with said second end being further provided with internal locking means, said internal locking means further comprising a constriction in the lumen at the second end of the proximal cannula;

(b) a distal cannula provided with a lumen, said distal cannula adapted to slide within said lumen of said proximal cannula in a telescopic relation, said distal cannula having first and second ends wherein said second end is closed and is provided with perforations, said first end having external locking means, said external locking means further comprising an annular outwardly radially extending lip;

(c) means, slideably received within the proximal cannula and extending to the distal cannula, for slideably adjusting the distal cannula within the proximal cannula, whereby one may set a desired length of the distal cannual extending beyond the second end of the proximal cannula with a maximum extension achieved by extending the second end of the distal cannula beyond the second end of the proximal cannula to a point where the internal locking means cooperates with the external locking means thereby preventing further extension, said means for adjusting the distal cannula further comprising a stylet adapted to fit within the lumens of the cannulas.

15. The device of claim 4 wherein said stylet is longer than the proximal and distal cannulas in maximum extension.

16. The device of claim 15 wherein said stylet further comprises first and second ends where said first end is provided with handle means and said second end is provided with extension and retraction means.

17. The device of claim 16 where said extension and retraction means further comprises raised projections on said second end of said stylet, whereby said projections may be manipulated to capture said perforations, whereby a sliding movement of said stylet within the proximal and distal cannulas effects a telescopic extension and retraction of said distal cannula within said proximal cannula.

18. The device of claim 1 where said first end of said proximal catheter further comprises an access port for receiving the insertion of said distal catheter first end first and the second end of the stylet, and a discharge port for draining of fluids out of the proximal catheter.

19. The device of claim 1 where said first end of said proximal catheter further comprises a reservoir upon which the discharge port and access port are located.

20. The device of claim 19 wherein said cannulas are made of thermoplastic material.

21. The device of claim 20 wherein said stylet is made of a flexible metal alloy.

22. A method for treatment of hydrocephalic patients comprising the steps of:

(a) Implanting an adjustable, ventricular catheter utilizing standard operative procedure;

(b) Adjusting the length of said catheter to meet attending circumstances;

(c) Draining fluid through said catheter, said step of draining being performed using an adjustable ventricular catheter having a proximal section and a distal section in a telescoping relationship, each section having a cannula, lumen, and first and second ends, wherein the proximal section is adapted to slideably receive the distal section and wherein the second end of the proximal section is provided with internal locking means and the first end of the distal section is provided with external locking means, and wherein the second end of the distal section is closed being further provided with perforations, said external locking means and internal locking means cooperating when said distal section is maximally extended telescopically within the proximal section, and where the step of adjusting is accomplished by way of an extension, retraction stylet having a handle on one end and radially outward extending projections on the other end whereby said adjusting stylet is inserted into the lumen at the first end of said proximal section with the end having the radial projections inserted first such that said projections capture said perforations and movement of said adjusting stylet within the lumens effects changes in the telescoping relationship between the proximal and distal sections of the adjustable ventricular catheter.

23. The method of claim 17 where the step of implanting utilizes an implantation stylet having a handle on one end and is adaptively inserted within the lumens of the proximal and distal sections.

24. The method of claim 22 where the step of implanting also utilizes a depth gauge which is a hollow tubular member corresponding to a desired length into which the implantation stylet fits.

* * * * *